United States Patent
Goto et al.

(10) Patent No.: US 7,135,582 B2
(45) Date of Patent: Nov. 14, 2006

(54) TRANSITION METAL COMPLEX HAVING DIPHOSPHINE COMPOUND AS LIGAND

(75) Inventors: Mitsutaka Goto, Osaka (JP); Mitsuhisa Yamano, Osaka (JP); Shinji Kawaguchi, Osaka (JP)

(73) Assignee: Takeda Pharmaceutiacal Company Limited, Osaka (JP)

( * ) Notice: Subject to any disclaimer, the term of this patent is extended or adjusted under 35 U.S.C. 154(b) by 40 days.

(21) Appl. No.: 10/536,731

(22) PCT Filed: Dec. 4, 2003

(86) PCT No.: PCT/JP03/15536

§ 371 (c)(1),
(2), (4) Date: May 27, 2005

(87) PCT Pub. No.: WO2004/050667

PCT Pub. Date: Jun. 17, 2004

(65) Prior Publication Data

US 2006/0094887 A1    May 4, 2006

(30) Foreign Application Priority Data

Dec. 5, 2002  (JP) .............................. 2002-354341

(51) Int. Cl.
*C07F 15/00*    (2006.01)
*C07C 29/14*    (2006.01)
*C07C 69/66*    (2006.01)
*C07D 307/02*   (2006.01)
*C07D 303/00*   (2006.01)

(52) U.S. Cl. ........................ 556/21; 560/179; 549/507; 549/513; 568/881

(58) Field of Classification Search ................... 556/21; 549/507, 513; 560/179; 568/881
See application file for complete search history.

(56) References Cited

U.S. PATENT DOCUMENTS

2003/0045727 A1    3/2003    Nakano et al.
2005/0027124 A1    2/2005    Goto et al.

FOREIGN PATENT DOCUMENTS

| EP | 0754696 A1 | * | 1/1997 |
| EP | 1452537 A1 | * | 9/2004 |
| JP | 2002/363160 | | 12/2002 |
| WO | WO98/42716 | * | 10/1998 |

* cited by examiner

Primary Examiner—Porfirio Nazario-Gonzalez

(57) ABSTRACT

A transition metal complex having 2,2'-bis[bis(3,5-di-tert-butyl-4-methoxyphenyl)phosphino]-1,1'-binaphthyl as a ligand. The presence of the transition metal complex in the reaction system of an asymmetric reaction system allows the preparation of an objective compound having an objective absolute configuration with improved efficiency.

18 Claims, No Drawings

TRANSITION METAL COMPLEX HAVING DIPHOSPHINE COMPOUND AS LIGAND

This application is the National Phase filing of International Patent Application No. PCT/JP03/15536, filed Dec. 4, 2003.

TECHNICAL FIELD

The present invention relates to a transition metal complex with 2,2'-bis[bis(3,5-di-tert-butyl-4-methoxyphenyl)phosphino]-1,1'-binaphthyl as a ligand, which can be a catalyst useful for various asymmetric synthesis reactions.

BACKGROUND ART

In asymmetric reduction, asymmetric isomerization and the like using a transition metal coordinated with optically active phosphine as a catalyst, 2,2'-bis(diphenylphosphino)-1,1'-binaphthyl (hereinafter, abbreviated as BINAP in some cases) is generally used as the optically active phosphine. However, reactions using BINAP may be poor in reactivity, stereoselectivity, catalyst efficiency or the like depending on the kind of a substrate. Therefore various optically active phosphines have been prepared and reported (e.g., see Handbook of Enantioselective Catalysis with Transition Metal Compounds, published by VCH in 1993). For example, JP-A 61-63690 discloses that a ruthenium complex with 2,2'-bis(di(p-tolyl)phosphino)-1,1'-binaphthyl as a ligand is useful for asymmetric reduction of a carbon-carbon double bond. JP-A 3-255090 discloses that a ruthenium complex with 2,2'-bis(di(3,5-dialkylphenyl)phosphino)-1,1'-binaphthyl as a ligand is useful for asymmetric reduction of β-ketoester.

However, reactions using these transition metal catalysts may be poor in optical selectivity in some cases depending on a reaction substrate.

DISCLOSURE OF INVENTION

The present invention provides a novel transition metal complex capable of providing good selectivity and a good conversion rate of a reaction substrate in various asymmetric synthesis reactions and having an ability to sustain the reactions.

The present inventors found that a transition metal complex with 2,2'-bis[bis(3,5-di-tert-butyl-4-methoxyphenyl)phosphino]-1,1'-binaphthyl represented by the following structural formula:

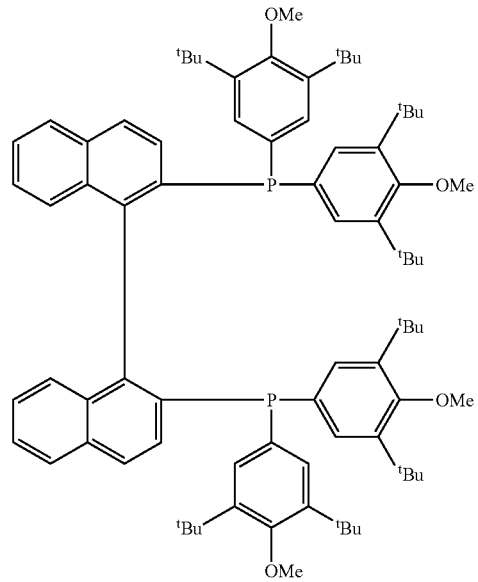

(hereinafter, abbreviated as Compound (I)) as a ligand provided good selectivity and a good conversion rate of a reaction substrate in asymmetric synthesis reaction, particularly asymmetric reduction, and then completed the present invention based on the finding.

That is, the present invention relates to:

[1] a transition metal complex with 2,2'-bis[bis(3,5-di-tert-butyl-4-methoxyphenyl)phosphino]-1,1'-binaphthyl as a ligand,

[2] the transition metal complex according to the above [1], wherein the transition metal is rhodium, ruthenium, iridium, palladium, nickel or copper,

[3] the transition metal complex according to the above [1], wherein the transition metal is rhodium, ruthenium, iridium, palladium or nickel,

[4] the transition metal complex according to the above [1], wherein the transition metal is rhodium,

[5] the transition metal complex according to the above [1], wherein the transition metal is ruthenium,

[6] the transition metal complex according to the above [1], which is represented by $Ru(L)(AcO)_2$ wherein L denotes 2,2'-bis[bis(3,5-di-tert-butyl-4-methoxyphenyl)phosphino]-1,1'-binaphthyl and Ac denotes acetyl,

[7] the transition metal complex according to the above [1], which is represented by $Ru(L)Cl_2$ wherein L denotes 2,2'-bis[bis(3,5-di-tert-butyl-4-methoxyphenyl)phosphino]-1,1'-binaphthyl,

[8] the transition metal complex according to the above [1], which is represented by $Ru(L)Cl_2(dmf)_n$ wherein L denotes 2,2'-bis[bis(3,5-di-tert-butyl-4-methoxyphenyl)phosphino]-1,1'-binaphthyl and dmf denotes N,N-dimethylformamide,

[9] the transition metal complex according to the above [1], which is represented by $[Rh(L)(cod)]OTf$ wherein L denotes 2,2'-bis[bis(3,5-di-tert-butyl-4-methoxyphenyl)phosphino]-1,1'-binaphthyl, cod denotes 1,5-cyclooctadiene, and Tf denotes trifluoromethylsulfonyl,

[10] a process for preparing a compound represented by the formula:

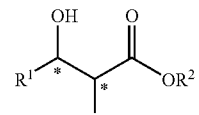

wherein * denotes the position of asymmetric carbon and the other symbols are as defined below, or a salt thereof, which comprises reducing a compound represented by the formula:

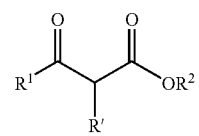

wherein $R^1$ denotes an optionally substituted hydrocarbon group or an optionally substituted heterocyclic group, R' denotes a halogen atom, optionally substituted alkylsulfonyloxy or optionally substituted arylsulfonyloxy, and R² denotes an optionally substituted hydrocarbon group, or a salt thereof in the presence of a transition metal complex with 2,2'-bis[bis(3,5-di-tert-butyl-4-methoxyphenyl)phosphino]-1,1'-binaphthyl as a ligand,

[11] a process for preparing a compound represented by the formula:

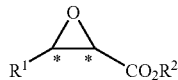

wherein respective symbols are as defined below, or a salt thereof, which comprises reducing a compound represented by the formula:

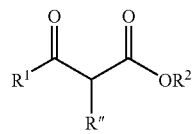

wherein R¹ denotes an optionally substituted hydrocarbon group or an optionally substituted heterocyclic group, R" denotes a chlorine atom, a bromine atom, an iodine atom, optionally substituted alkylsulfonyloxy or optionally substituted arylsulfonyloxy, and R² denotes an optionally substituted hydrocarbon group, or a salt thereof in the presence of a transition metal complex in a solvent selected from an alcohol solvent, a hydrocarbon solvent, an ether solvent, an ester solvent, a ketone solvent, a nitrile solvent, a sulfoxide solvent and an amide solvent, or a mixed solvent of two or more kinds of them, to obtain a compound represented by the formula:

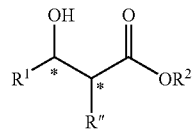

wherein * denotes the position of asymmetric carbon and the other symbols are as defined above, or a salt thereof, and then cyclizing the resulting compound in the presence of an inorganic base,

[12] the process according to the above [11], wherein the compound represented by the formula:

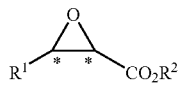

wherein R¹ denotes an optionally substituted hydrocarbon group or an optionally substituted heterocyclic group, R² denotes an optionally substituted hydrocarbon group, and * denotes the position of asymmetric carbon, is an optically active compound represented by the formula:

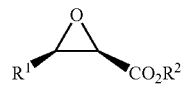

wherein respective symbols are as defined above, or the formula:

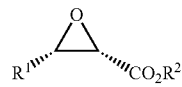

wherein respective symbols are as defined above,

[13] the process according to the above [11], wherein the compound represented by the formula:

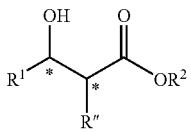

wherein R¹ denotes an optionally substituted hydrocarbon group or an optionally substituted heterocyclic group, R" denotes a chlorine atom, a bromine atom, an iodine atom, optionally substituted alkylsulfonyloxy or optionally substituted arylsulfonyloxy, R² denotes an optionally substituted hydrocarbon group, and * denotes the position of asymmetric carbon, is an optically active compound represented by the formula:

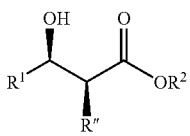

wherein respective symbols are as defined above, or the formula:

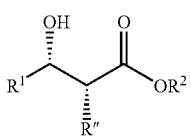

wherein respective symbols are as defined above,

[14] the process according to the above [11], wherein R" is a chlorine atom, a bromine atom or an iodine atom,

[15] the process according to the above [11], wherein the inorganic base is alkali metal carbonate,

[16] the process according to the above [11], wherein the solvent for reduction is an alcohol solvent,

[17] the process according to the above [11], wherein the transition metal complex is a transition metal complex with 2,2'-bis[bis(3,5-di-tert-butyl-4-methoxyphenyl)phosphino]-1,1'-binaphthyl as a ligand, Compound (I) includes the (R)-form, the (S)-form and a mixture of the (R)-form and the (S)-form (the mixing ratio is not limited), and the optically active forms are preferred.

A process for preparing Compound (I) will be shown below.

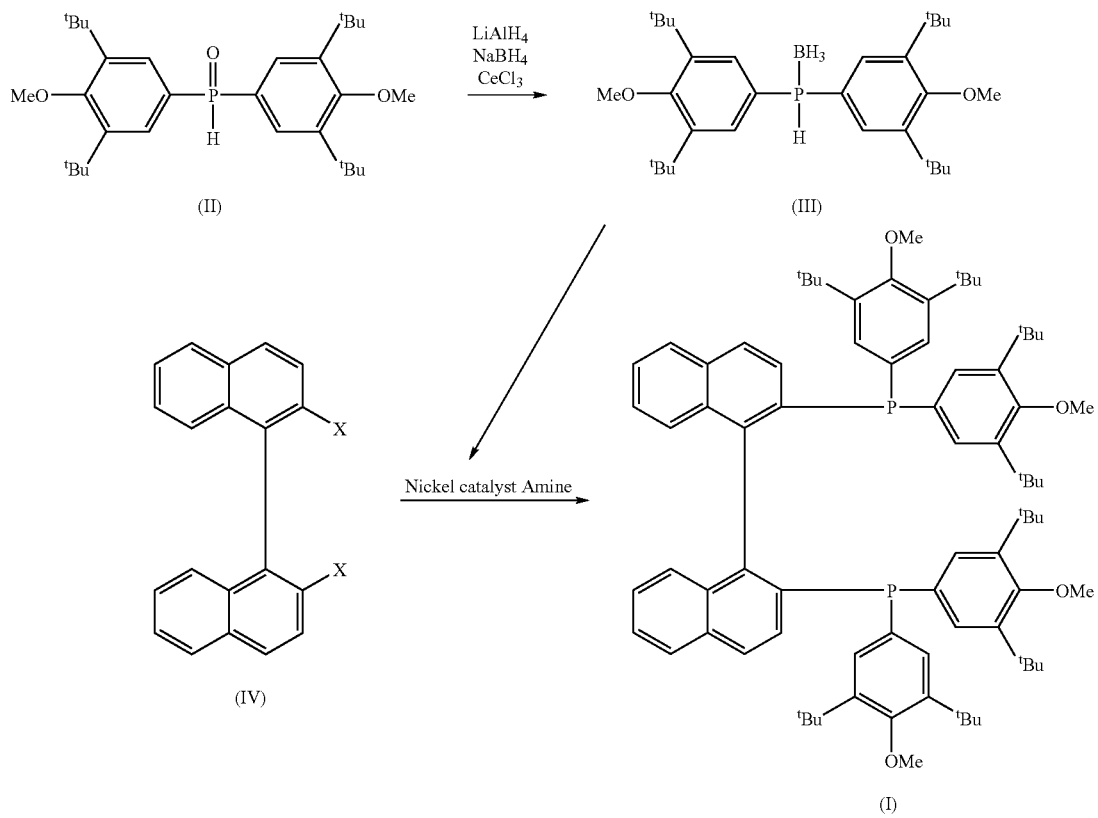

[18] a process for preparing a compound represented by the formula:

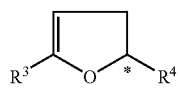

wherein * denotes the position of asymmetric carbon and the other symbols are as defined below, or a salt thereof, which comprises reacting a compound represented by the formula:

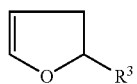

wherein $R^3$ denotes a hydrogen atom or optionally substituted alkyl, or a salt thereof with a compound represented by the formula: $R^4$—R''' wherein $R^4$ denotes optionally substituted phenyl and R''' denotes a leaving group, or a salt thereof in the presence of a transition metal complex with 2,2'-bis[bis(3,5-di-tert-butyl-4-methoxyphenyl)phosphino]-1,1'-binaphthyl as a ligand, and the like.

wherein X denotes a leaving group such as bromine, iodide, trifluoromethanesulfonyloxy or methanesulfonyloxy.

Compound (II) can be prepared according to a method described in Journal of Organic Chemistry, vol. 33, p. 3690, 1968.

Compound (III) can be prepared by reacting Compound (II) in the presence of cerium chloride, sodium borohydride and lithium aluminum hydride.

The amount of cerium chloride to be used is about 1 to 6 mol, preferably about 3 to 5 mol per 1 mol of Compound (II).

The amount of sodium borohydride to be used is about 2 to 10 mol, preferably about 3 to 5 mol per 1 mol of Compound (II).

The amount of lithium aluminum hydride to be used is about 0.25 to 5 mol, preferably about 1 to 3 mol per 1 mol of Compound (II).

The above reaction can be performed in an inert organic solvent. Examples of the organic solvent include hydrocarbon solvents (e.g., hexane, pentane, cyclohexane, etc.), amide solvents (e.g., N,N-dimethylformamide (DMF), N,N-dimethylacetamide, N-methylpyrrolidone, 1,3-dimethyl-2-imidazolidinone, etc.), aromatic hydrocarbon solvents (e.g., toluene, benzene, chlorobenzene, etc.), ether solvents (e.g., diisopropyl ether, diethyl ether, tetrahydrofuran (THF), 1,4-dioxane, 1,2-dimethoxyethane, etc.), and phosphoric amide solvents (e.g., hexamethylphosphoric amide, etc.). These solvents may be used alone or as a mixed solvent. Preferred are ether solvents, hydrocarbon solvents, and aromatic hydrocarbon solvents. More preferred are ether solvents (e.g., diisopropyl ether, diethyl ether, tetrahydrofuran (THF), 1,4-dioxane, 1,2-dimethoxyethane, etc).

The reaction temperature of the reaction is about −20 to 50° C., preferably about −10 to 35° C. The reaction time of the reaction is about 1 to 48 hours, preferably 1 to 20 hours.

Compound (IV) can be prepared according to a method known per se, for example, a method described in Tetrahedron Letters, vol. 31, p. 985, 1990, Journal of Organic Chemistry, vol. 58, p. 1945, 1993, or the like. Compound (IV) thus obtained may be used as a reaction mixture without isolation in a reaction with Compound (III).

Compound (I) can be prepared by reacting Compound (III) and Compound (IV) in the presence of amine and a nickel catalyst in a solvent.

Examples of the "amine" to be used include 1,4-diazabicyclo[2.2.2]octane (abbreviation: DABCO), triethylamine, diisopropylethylamine, tri(n-propyl)amine, tri(n-butyl)amine, 1,8-diazabicyclo[5.4.0]-7-undecene (abbreviation: DBU), tetramethylethylenediamine, dimethylaniline, 1,4-dimethylpiperazine, 1-methylpiperidine, 1-methylpyrrolidine, 4-dimethylaminopyridine, pyridine, and diethylamine. Among them, preferred are tertiary amines such as 1,4-diazabicyclo[2.2.2]octane, triethylamine and diisopropylethylamine. Particularly preferred is 1,4-diazabicyclo[2.2.2] octane.

Examples of the "nickel catalyst" to be used include $NiCl_2$.bis(diphenyl)phosphino $C_{1-4}$ alkane, $NiBr_2$, $NiCl_2$, $NiCl_2$.bis(diphenyl)phosphinylferrocene, $NiCl_2$.bis(triphenylphosphine), Ni.tetrakistriphenylphosphine, Ni.tetrakistriphenylphosphite, Ni.dicarbonylbis(triphenyl)phosphine, $NiBr_2$.bis(triphenylphosphine), Ni.bis(1,5-cyclooctadiene), Ni.bis(cyclopentadienyl), Ni.bis(ethylcyclopentadienyl), $NiCl_2$.dimethoxyethane, $Ni(BF_4)_2$ and $Ni(PF_3)_4$. Among them, $NiCl_2$.bis(diphenyl)phosphino $C_{1-4}$ alkane, $NiBr_2$, $NiCl_2$, $NiCl_2$.bis(diphenyl)phosphinylferrocene, $NiCl_2$.bis(triphenylphosphine), Ni.tetrakistriphenylphosphine, Ni.tetrakistriphenylphosphite and Ni.dicarbonylbis(triphenyl) phosphine are preferred. Inter alia, $NiCl_2$.bis(diphenyl) phosphino $C_{1-4}$ alkane is preferred, and $NiCl_2$.bis(diphenyl) phosphinoethane is particularly preferred.

The amount of Compound (III) to be used is about 2 to 5 mol, preferably about 2 to 3 mol per 1 mol of Compound (IV).

The amount of amine to be used is about 2 to 10 mol, preferably about 2 to 8 mol per 1 mol of Compound (IV).

The amount of a nickel catalyst to be used is about 0.01 to 10 mol, preferably about 0.05 to 1 mol per 1 mol of Compound (IV).

The above reaction can be performed in an inert organic solvent. Examples of the organic solvent include hydrocarbon solvents (e.g., hexane, pentane, cyclohexane, etc.), amide solvents (e.g., N,N-dimethylformamide (DMF), N,N-dimethylacetamide, N-methylpyrrolidone, 1,3-dimethyl-2-imidazolidinone, etc.), aromatic hydrocarbon solvents (e.g., toluene, benzene, chlorobenzene, etc.), aliphatic ester solvents (e.g., ethyl acetate, n-propyl acetate, n-butyl acetate, etc.), ether solvents (e.g., diisopropyl ether, diethyl ether, tetrahydrofuran (THF), 1,4-dioxane, 1,2-dimethoxyethane, etc.), halogenated hydrocarbon solvents (e.g., chloroform, dichloromethane, 1,2-dichloroethane, carbon tetrachloride, etc.), alcohol solvents (e.g., methanol, ethanol, isopropanol, tert-butanol, etc.), ketone solvents (e.g., acetone, ethyl methyl ketone, etc.), sulfoxide solvents (e.g., dimethyl sulfoxide, etc.), nitrile solvents (e.g., acetonitrile, propionitrile, etc.), and phosphoric amide solvents (e.g., hexamethylphosphoric amide, etc.). These solvents may be used alone, or as a mixed solvent. Preferred are amide solvents, sulfoxide solvents, and phosphoric amide solvents. More preferred are amide solvents (N,N-dimethylformamide (DMF), N,N-dimethylacetamide, N-methylpyrrolidone, 1,3-dimethyl-2-imidazolidinone).

The reaction temperature of the reaction is about 30 to 180° C., preferably about 80 to 120° C. The reaction time of the reaction is about 1 to 240 hours, preferably about 24 to 168 hours.

The product may be isolated from the reaction mixture according to a conventional method, and can be easily purified by a separation means such as recrystallization, distillation or chromatography.

The "transition metal" of the transition metal complex of the present invention includes rhodium, ruthenium, iridium, palladium, nickel, and copper. Inter alia, rhodium and ruthenium are preferred.

The transition metal complex of the present invention can be prepared by a known method.

For example, when a rhodium complex is prepared, it can be prepared by reacting Compound (I) with bis(cycloocta-1,5-diene)rhodium(I) tetrafluoroborate according to a method described in "4$^{th}$ edition Jikken Kagaku Koza (Experimental Chemistry Course)", vol. 18, Organometal Complex, p. 341–344, 1991 edited by Japan Chemistry Society (Maruzen).

When a ruthenium complex is prepared, it can be prepared by heating Compound (I) and $[Ru(cod)Cl_2]_n$ under reflux in the presence of triethylamine in a toluene solvent according to a method described in J. Chem. Soc., Chem. Commun., P. 922, 1988. Alternatively, it can be prepared by heating Compound (I) and $[Ru(p\text{-cymene})I_2]_2$ under stirring in methylene chloride and ethanol according to a method described in J. Chem. Soc., Chem. Commun., P. 1208, 1989.

When an iridium complex is prepared, it can be prepared by reacting Compound (I) and $[Ir(cod)(CH_3CN)_2]BF_4$ under stirring in tetrahydrofuran according to a method described in J. Organomet. Chem., vol. 428, p. 213, 1992.

When a palladium complex is prepared, it can be prepared by reacting Compound (I) and π-allylpalladium chloride according to a method described in J. Am. Chem. Soc., vol. 113, p. 9887, 1991.

When a nickel complex is prepared, it can be prepared by heating and stirring Compound (I) and nickel chloride in the presence of a solvent according to a method described in "4$^{th}$ Jikken Kagaku Koza", vol. 18, Organometal Complex, p. 376 (1991) edited by Japan Chemistry Society (Maruzen).

When a copper complex is prepared, it is prepared by reacting Compound (I) and copper(I) chloride according to a method described in "4$^{th}$ Jikken Kagaku Koza", vol. 18, Organometal Complex, p. 444 (1991) edited by Japan Chemistry Society (Maruzen).

Specific examples of the rhodium complex include the following complexes (in the following formulas of a transition metal complex, L denotes Compound (I) of the present invention, cod denotes 1,5-cyclooctadiene, Tf denotes trifluoromethylsulfonyl, nbd denotes norbornadiene, Ph denotes phenyl, Ac denotes acetyl, Et denotes ethyl, dmf denotes N,N-dimethylformamide, en denotes ethylenediamine, dpen denotes 1,2-diphenylethylenediamine, daipen denotes 1,1-di(4-anisyl)-2-isopropyl-1,2-ethylenediamine, and n denotes 1 or more):

[Rh(cod)(L)]OTf, Rh(L)Cl, Rh(L)Br, Rh(L)I, [Rh(cod)(L)]$BF_4$, [Rh(cod)(L)]$ClO_4$, [Rh(cod)(L)]$PF_6$, [Rh(cod)(L)]$BPh_4$, [Rh(nbd)(L)]OTf, [Rh(nbd)(L)]$BF_4$, [Rh(nbd)(L)]$ClO_4$, [Rh(nbd)(L)]$PF_6$, [Rh(nbd)(L)]$BPh_4$, [Rh(L)($CH_3OH$)$_2$]OTf, [Rh(L)($CH_3OH$)$_2$]$BF_4$, [Rh(L)($CH_3OH$)$_2$]$ClO_4$, [Rh(L)($CH_3OH$)$_2$]$PF_6$, [Rh(L)($CH_3OH$)$_2$]$BPh_4$.

Specific examples of the ruthenium complex include the following complexes:

$RuCl_2(L)$, $RuBr_2(L)$, $RuI_2(L)$, $Ru(OAc)_2(L)$, $Ru(O_2CCF_3)_2(L)$, $[NH_2Et_2][\{RuCl(L)\}_2(\mu\text{-}Cl)_3]$, $[Ru_2Cl_4(L)](NEt_3)$, $Ru(L)Cl_2(dmf)_n$, $Ru(L)(methylallyl)_2$, [RuCl(benzene)(L)]Cl, [RuCl(benzene)(L)]Br, [RuCl(benzene)(L)]I, [RuCl(benzene)(L)]OTf, $[RuCl(benzene)(L)]ClO_4$, $[RuCl(benzene)(L)]PF_6$, $[RuCl(benzene)(L)]BF_4$, $[RuCl(benzene)(L)]BPh_4$, [RuBr(benzene)(L)]Cl, [RuBr(benzene)(L)]Br, [RuBr(benzene)(L)]I, [RuI(benzene)(L)]Cl, [RuI(benzene)(L)]Br, [RuI(benzene)(L)]I, [RuCl(p-cymene)(L)]Cl, [RuCl(p-cymene)(L)]Br, [RuCl(p-cymene)(L)]I, [RuBr(p-cymene)(L)]Cl, [RuBr(p-cymene)(L)]Br, [RuBr(p-cymene)(L)]I, [RuI(p-cymene)(L)]Cl, [RuI(p-cymene)(L)]Br, [RuI(p-cymene)(L)]I, $[Ru(L)](OTf)_2$, $[Ru(L)](BF_4)_2$, $(Ru(L)](ClO_4)_2$, $[Ru(L)](PF_6)_2$, $[Ru(L)](BPh_4)_2$, $[RuH(L)_2]Cl$, $[RuH(L)_2]OTf$, $[RuH(L)_2]BF_4$, $[RuH(L)_2]ClO_4$, $[RuH(L)_2]PF_6$, $[RuH(L)_2]BPh_4$, $(RuH(CH_3CN)(L)]Cl$, $[RuH(CH_3CN)(L)]OTf$, $[RuH(CH_3CN)(L)]BF_4$, $[RuH(CH_3CN)(L)]ClO_4$, $[RuH(CH_3CN)(L)]PF_6$, $[RuH(CH_3CN)(L)]BPh_4$, [Ru(L)Cl]OTf, $[Ru(L)Cl]BF_4$, $[Ru(L)Cl]ClO_4$, $[Ru(L)Cl]PF_6$, $[Ru(L)Cl]BPh_4$, [Ru(L)Br]OTf, $[Ru(L)Br]BF_4$, $[Ru(L)Br]ClO_4$, $[Ru(L)Br]PF_6$, $[Ru(L)Br]BPh_4$, [Ru(L)I]OTf, $[Ru(L)I]BF_4$, $[Ru(L)I]ClO_4$, $[Ru(L)I]PF_6$, $[Ru(L)I]BPh_4$, $RuCl_2(L)(en)$, $RuCl_2(L)(dpen)$, $RuCl_2(L)(daipen)$, $RuH(BH_4)(L)(en)$, $RuH(BH_4)(L)(daipen)$, $RuH(BH_4)(L)(dpen)$.

Specific examples of the iridium complex include the following complexes:

Ir(L)Cl, Ir(L)Br, Ir(L)I, [Ir(cod)(L)]OTf, $[Ir(cod)(L)]BF_4$, $[Ir(cod)(L)]ClO_4$, $[Ir(cod)(L)]PF_6$, $[Ir(cod)(L)]BPh_4$, [Ir(nbd)(L)]OTf, $[Ir(nbd)(L)]BF_4$, $[Ir(nbd)(L)]ClO_4$, $[Ir(nbd)(L)]PF_6$, $[Ir(nbd)(L)]BPh_4$.

Specific examples of the palladium complex include the following complexes:

$PdCl_2(L)$, $PdBr_2(L)$, $PdI_2(L)$, $(\pi\text{-allyl})Pd(L)$, [Pd(L)]OTf, $[Pd(L)]BF_4$, $[Pd(L)]ClO_4$, $[Pd(L)]PF_6$, $[Pd(L)]BPh_4$.

Specific examples of the nickel complex include the following complexes:

$NiCl_2(L)$, $NiBr_2(L)$, $NiI_2(L)$, $(\pi\text{-allyl})Ni(L)$.

Specific examples of the copper complex include the following complexes:

CuCl(L), CuBr(L), CuI(L), CuH(L), $Cu(BH_4)(L)$, $Cu(C_5H_5)(L)$, $Cu(C_5(CH_3)_5)(L)$.

Among the transition metal complexes of the present invention, particularly preferred are $Ru(L)(AcO)_2$, $Ru(L)Cl_2$, $Ru(L)Cl_2(dmf)_n$ and [Rh(L)(cod)]OTf.

It is possible to prepare a compound having the objective configuration by using the transition metal complex of the present invention in reduction, Heck reaction or the like. Examples of the reaction will be shown below.

1. Asymmetric Reduction of β-ketoester

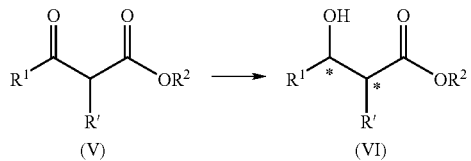

(V)    (VI)

wherein $R^1$ denotes an optionally substituted hydrocarbon group or an optionally substituted heterocyclic group, R' denotes a halogen atom, optionally substituted alkylsulfonyloxy or optionally substituted arylsulfonyloxy, and $R^2$ denotes an optionally substituted hydrocarbon group.

An optically active compound (VI) can be obtained by subjecting Compound (V) to hydrogenation reaction in the presence of the transition metal complex of the present invention.

The hydrocarbon group of "an optionally substituted hydrocarbon group" represented by $R^1$ and $R^2$ includes alkyl (e.g., $C_{1-6}$ alkyl such as methyl, ethyl, propyl, isopropyl, butyl, isobutyl, sec-butyl, tert-butyl, pentyl, hexyl, etc.), cycloalkyl (e.g., $C_{3-8}$ cycloalkyl such as cyclopropyl, cyclobutyl, cyclopentyl, cyclohexyl, cycloheptyl, cyclooctyl, etc.), aryl (e.g., $C_{6-10}$ aryl such as phenyl, 1-naphthyl, 2-naphthyl, etc.), and aralkyl (e.g., $C_{7-11}$ aralkyl such as benzyl, phenylethyl, phenylpropyl, 1-naphthylmethyl, 2-naphthylmethyl, etc.).

A substituent for "an optionally substituted hydrocarbon group" represented by $R^1$ and $R^2$ includes hydroxy, alkoxy (e.g., $C_{1-6}$ alkoxy such as methoxy, ethoxy, propoxy, isopropoxy, butoxy, isobutoxy, sec-butoxy, tert-butoxy, pentoxy, hexyloxy, etc.), formyl, alkylcarbonyl (e.g., $C_{1-6}$ alkyl-carbonyl such as acetyl, propionyl, butyryl, isobutyryl, valeryl, isovaleryl, pivaloyl, etc.), alkoxycarbonyl (e.g., $C_{1-6}$ alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl, etc.), carboxyl, N-mono lower alkylcarbamoyl (e.g., N-mono $C_{1-6}$ alkylcarbamoyl such as N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, etc.), N,N-di lower alkylcarbamoyl (e.g., N,N-di $C_{1-6}$alkyl-carbamoyl such as N,N-dimethylcarbamoyl, N,N-diethylcarbamoyl, N,N-dipropylcarbamoyl, N,N-diisopropylcarbamoyl, N-ethyl-N-methylcarbamoyl, etc.), and a halogen atom (e.g., a fluorine atom, a chlorine atom, a bromine atom, and an iodine atom). The optionally substituted hydrocarbon group may have 1 to 3 substituents selected from the above-mentioned substituents at replaceable positions.

The heterocyclic group of "an optionally substituted heterocyclic group" represented by $R^1$ includes 5- to 14-membered heterocyclic groups containing 1 to 4 of one or two kinds of heteroatoms selected from a nitrogen atom, a sulfur atom and an oxygen atom in addition to carbon atoms (e.g., aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; non-aromatic heterocyclic groups such as 2-pyrrolidinyl, 3-pyrrolidinyl, 2-imidazolinyl, 4-imidazolinyl, 3-pyrazolidinyl, 4-pyrazolidinyl, 2-piperidyl, 3-piperidyl, 4-piperidyl, 2-piperazinyl, etc.).

A substituent for "an optionally substituted heterocyclic group" represented by $R^1$ includes hydroxy, alkoxy (e.g., $C_{1-6}$ alkoxy such as methoxy, ethoxy, propoxy, isopropoxy, butoxy, isobutoxy, sec-butoxy, tert-butoxy, pentoxy, hexyloxy, etc), formyl, alkylcarbonyl (e.g., $C_{1-6}$ alkyl-carbonyl such as acetyl, propionyl, butyryl, isobutyryl, valeryl, isovaleryl, pivaloyl, etc.), alkoxycarbonyl (e.g., $C_{1-6}$ alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl, etc.), carboxyl, N-mono lower alkylcarbamoyl (e.g., N-mono $C_{1-6}$ alkylcarbamoyl such as N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, etc.), N,N-di lower alkylcarbamoyl (e.g., N,N-di $C_{1-6}$alkyl-carbamoyl such as N,N-dimethylcarbamoyl, N,N-diethylcarbamoyl, N,N-dipropylcarbamoyl, N,N-diisopropylcarbamoyl, N-ethyl-N-methylcarbamoyl, etc.), and a halogen atom (e.g., a fluorine atom, a chlorine atom, a bromine atom, and an iodine atom). The optionally substituted heterocyclic group may have 1 to 3 substituents selected from the above-mentioned substituents at replaceable positions.

$R^1$ is preferably aryl, and more preferably phenyl.

$R^2$ is preferably alkyl, and more preferably ethyl.

"A halogen atom" represented by R' includes a fluorine atom, a chlorine atom, a bromine atom, and an iodine atom.

The "alkylsulfonyloxy" of "an optionally substituted alkylsulfonyloxy" represented by R' includes $C_{1-4}$ alkylsulfonyloxy such as methylsulfonyloxy, ethylsulfonyloxy, propylsulfonyloxy, isopropylsulfonyloxy, butylsulfonyloxy, isobutylsulfonyloxy, sec-butylsulfonyloxy, tert-butylsulfonyloxy and the like.

A substituent for "an optionally substituted alkylsulfonyloxy" represented by R' includes a halogen atom (e.g., a fluorine atom, a chlorine atom, a bromine atom, and an iodine atom) and the like.

The "arylsulfonyloxy" of "an optionally substituted arylsulfonyloxy" represented by R' includes $C_{6-10}$ arylsulfonyloxy such as phenylsulfonyloxy, 1-naphthylsulfonyloxy, 2-naphthylsulfonyloxy and the like.

A substituent for "an optionally substituted arylsulfonyloxy" represented by R' includes a halogen atom (e.g., a fluorine atom, a chlorine atom, a bromine atom, and an iodine atom), alkyl (e.g., $C_{1-6}$ alkyl such as methyl, ethyl, propyl, isopropyl, butyl, isobutyl, sec-butyl, tert-butyl, pentyl, hexyl, etc.) optionally having a halogen atom (e.g., a fluorine atom, a chlorine atom, a bromine atom, and an iodine atom) and the like.

R' is preferably a chlorine atom, a bromine atom or an iodine atom, and more preferably a chlorine atom.

In the asymmetric reduction of Compound (V), the amount of the transition metal complex of the present invention to be used is about 0.01 mmol to about 1 mol, preferably about 1 mmol to about 10 mmol per 1 mol of Compound (V).

In the asymmetric reduction of Compound (V), hydrogen gas is used as a hydrogen source. The hydrogen pressure of the reaction is about 0.1 MPa to 10 MPa, preferably about 0.8 MPa to 5 MPa.

The asymmetric reduction of Compound (V) is performed in a solvent. Examples of the solvent to be used include alcohol solvents (e.g., methanol, ethanol, n-propanol, isopropanol, etc.), hydrocarbon solvents (e.g., hexane, benzene, toluene, xylene, etc.), ether solvents (e.g., diethyl ether, diisopropyl ether, tert-butyl methyl ether, dioxane, tetrahydrofuran, etc.), ester solvents (e.g., ethyl acetate, isopropyl acetate), ketone solvents (e.g., acetone, methyl ethyl ketone, etc.), nitrile solvents (e.g., acetonitrile, propionitrile, etc.), sulfoxide solvents (e.g., dimethyl sulfoxide, etc.) and amide solvents (e.g., N,N-dimethylformamide, etc.), and a mixed solvent of two or more kinds of these solvents. Inter alia, alcohol solvents (e.g., methanol, ethanol, n-propanol, isopropanol, etc.) are preferred, and ethanol is particularly preferred.

The reaction temperature of the asymmetric reduction reaction of Compound (V) is about 0° C. to about 180° C., preferably about 20° C. to about 100° C.

The optically active compound (VI) obtained by the asymmetric reduction of Compound (V) has four stereostructural formulas of:

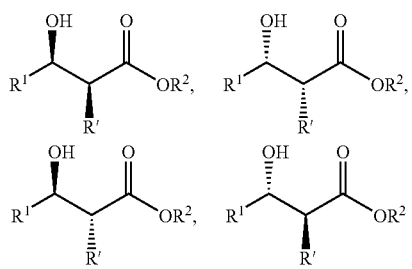

wherein respective symbols are as defined above. The compound (syn form) having the stereostructural formula:

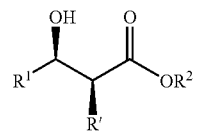

wherein respective symbols are as defined above, or the stereostructural formula:

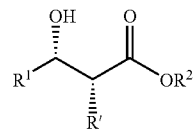

wherein respective symbols are as defined above, can be preferentially obtained.

Alternatively, the asymmetric reduction of Compound (V) may be performed using a transition metal complex which is usually used other than the transition metal complex of the present invention, under the same condition. Examples of a transition metal complex other than that of the present invention include transition metal complexes in which a transition metal is rhodium, ruthenium, nickel or cobalt.

Among Compound (VI), Compound (VI') in which R' is a chlorine atom, a bromine atom, an iodine atom, optionally substituted alkylsulfonyl or optionally substituted arylsulfonyl can be subjected to cyclization to obtain Compound (VII) which is useful as an intermediate for producing pharmaceuticals.

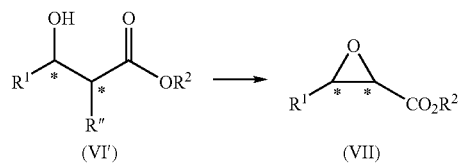

wherein R" is a chlorine atom, a bromine atom, an iodine atom, optionally substituted alkylsulfonyl or optionally substituted arylsulfonyl, and other respective symbols are as defined above.

The cyclization of Compound (VI') is performed in the presence of an inorganic base in a solvent.

Examples of an inorganic base used in the cyclization of Compound (VI') include alkali metal carbonate (e.g., sodium carbonate, potassium carbonate, etc.), alkaline earth metal carbonate (e.g., magnesium carbonate, calcium carbonate, etc.), alkali metal hydroxide (e.g., sodium hydroxide, potassium hydroxide, etc.), alkali metal phosphate (e.g., tripotassium phosphate, etc.), alkali metal bicarbonate (e.g., sodium hydrogen carbonate, potassium hydrogen carbonate, etc.) and the like. Inter alia, alkali metal carbonate (e.g., sodium carbonate, potassium carbonate, etc.) is preferred.

In the cyclization of Compound (VI'), the amount of the inorganic base to be used is about 1 mol to about 10 mol, preferably about 2 mol to about 4 mol per 1 mol of Compound (VI').

Examples of a solvent used in the cyclization of Compound (VI') include alcohol solvents (e.g., methanol, ethanol, n-propanol, isopropanol, etc.), hydrocarbon solvents (e.g., hexane, benzene, toluene, xylene, etc.), halogenated hydrocarbon solvents (e.g., dichloromethane, chloroform, 1,2-dichloroethane, etc.), ether solvents (e.g., diethyl ether, diisopropyl ether, tert-butyl methyl ether, dioxane, tetrahydrofuran, etc.), ester solvents (e.g., ethyl acetate, isopropyl acetate), ketone solvents (e.g., acetone, methyl ethyl ketone, etc.), nitrile solvents (e.g., acetonitrile, propionitrile, etc.), sulfoxide solvents (e.g., dimethyl sulfoxide, etc.), water and amide solvents (e.g., N,N-dimethylformamide, etc.), and a mixed solvent of two or more kinds of these solvents. Inter alia, sulfoxide solvents (e.g., dimethyl sulfoxide, etc.) and amide solvents (e.g., N,N-dimethylformamide, etc.) are preferred.

The reaction temperature of the cyclization of Compound (VI') is about −50° C. to about 180° C., preferably about 0° C. to about 100° C.

2. Heck Reaction

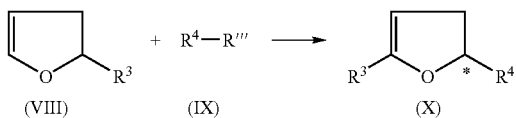

wherein $R^3$ denotes a hydrogen atom or optionally substituted alkyl, $R^4$ denotes optionally substituted phenyl, and $R'''$ denotes a leaving group.

By reacting Compound (VIII) with Compound (IX) in the presence of the transition metal complex of the present invention, an optically active compound (X) which is useful as an intermediate for producing pharmaceuticals can be obtained.

The "optionally substituted alkyl" represented by $R^3$ includes $C_{1-6}$ alkyl (e.g., methyl, ethyl, propyl, isopropyl, butyl, isobutyl, sec-butyl, tert-butyl, pentyl, hexyl, etc.) which optionally may have at replaceable positions 1 to 3 substituents selected from hydroxy, alkoxy (e.g., $C_{1-6}$ alkoxy such as methoxy, ethoxy, propoxy, isopropoxy, butoxy, isobutoxy, sec-butoxy, tert-butoxy, pentoxy, and hexyloxy), formyl, alkylcarbonyl (e.g., $C_{1-6}$ alkyl-carbonyl such as acetyl, propionyl, butyryl, isobutyryl, valeryl, isovaleryl, and pivaloyl), alkoxycarbonyl (e.g., $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, and hexyloxycarbonyl), carboxyl, N-mono lower alkylcarbamoyl (e.g., N-mono $C_{1-6}$ alkyl-carbamoyl such as N-methylcarbamoyl, N-ethylcarbamoyl, N-propylcarbamoyl, N-isopropylcarbamoyl, N-butylcarbamoyl, N-isobutylcarbamoyl, and N-tert-butylcarbamoyl), N,N-di lower alkylcarbamoyl (e.g., N,N-di $C_{1-6}$ alkyl-carbamoyl such as N,N-dimethylcarbamoyl, N,N-diethylcarbamoyl, N,N-dipropylcarbamoyl, N,N-diisopropylcarbamoyl, and N-ethyl-N-methylcarbamoyl) and the like.

$R^3$ is preferably a hydrogen atom.

A substituent for "optionally substituted phenyl" represented by $R^4$ includes hydroxy, alkoxy (e.g., $C_{1-6}$ alkoxy such as methoxy, ethoxy, propoxy, isopropoxy, butoxy, isobutoxy, sec-butoxy, tert-butoxy, pentoxy, and hexyloxy), formyl, alkylcarbonyl (e.g., $C_{1-6}$ alkyl-carbonyl such as acetyl, propionyl, butyryl, isobutyryl, valeryl, isovaleryl, and pivaloyl), alkoxycarbonyl (e.g., $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, and hexyloxycarbonyl), carboxyl, N-mono lower alkylcarbamoyl (e.g., N-mono $C_{1-6}$alkyl-carbamoyl such as N-methylcarbamoyl, N-ethylcarbamoyl, N-propylcarbamoyl, N-isopropylcarbamoyl, N-butylcarbamoyl, N-isobutylcarbamoyl, and N-tert-butylcarbamoyl), N,N-di lower alkylcarbamoyl (e.g., N,N-di $C_{1-6}$alkyl-carbamoyl such as N,N-dimethylcarbamoyl, N,N-diethylcarbamoyl, N,N-dipropylcarbamoyl, N,N-diisopropylcarbamoyl and N-ethyl-N-methylcarbamoyl), a halogen atom (e.g., a fluorine atom, a chlorine atom, a bromine atom, and an iodine atom) and cyano. The number of the substituents is 1 to 3.

$R^4$ is preferably unsubstituted phenyl.

"A leaving group" represented by $R'''$ includes a halogen atom, optionally substituted alkylsulfonyloxy, optionally substituted arylsulfonyloxy and the like. Examples of the "halogen atom", the "optionally substituted alkylsulfonyloxy" and the "optionally substituted arylsulfonyloxy" are the same as those of the "halogen atom", the "optionally substituted alkylsulfonyloxy" and the "optionally substituted arylsulfonyloxy" represented by $R'$. Inter alia, alkylsulfonyloxy optionally having a halogen atom is preferred, and trifluoromethylsulfonyloxy is particularly preferred.

The Heck reaction of Compound (VIII) and Compound (IX) is usually performed in a solvent. Examples of the solvent to be used include alcohol solvents (e.g., methanol, ethanol, n-propanol, isopropanol, etc.), hydrocarbon solvents (e.g., hexane, benzene, toluene, xylene, etc.), halogenated hydrocarbon solvents (e.g., dichloromethane, chloroform, 1,2-dichloroethane, etc.), ether solvents (e.g., diethyl ether, diisopropyl ether, tert-butyl methyl ether, dioxane, tetrahydrofuran, etc.), ester solvents (e.g., ethyl acetate, isopropyl acetate), ketone solvents (e.g., acetone, methyl ethyl ketone, etc.), nitrile solvents (e.g., acetonitrile, propionitrile, etc.), sulfoxide solvents (e.g., dimethyl sulfoxide, etc.) and amide solvents (e.g., N,N-dimethylformamide, etc.), and a mixed solvent of two or more kinds of these solvents. Inter alia, hydrocarbon solvents (e.g., hexane, benzene, toluene, xylene, etc.), ether solvents (e.g., diethyl ether, diisopropyl ether, tert-butyl methyl ether, dioxane, tetrahydrofuran, etc.) and amide solvents (e.g., N,N-dimethylformamide, etc.) are preferred. Ether solvents (e.g., diethyl ether, diisopropyl ether, tert-butyl methyl ether, dioxane, tetrahydrofuran, etc.) are more preferred.

The amount of the transition metal complex of the present invention used in the Heck reaction of Compound (VIII) and Compound (IX) is about 0.01 mmol to about 1 mol, preferably about 0.01 mol to about 0.1 mol per 1 mol of Compound (IX).

The amount of Compound (VIII) used in the Heck reaction of Compound (VIII) and Compound (IX) is about 1 mol to about 10 mol, preferably about 3 mol to about 5 mol per 1 mol of Compound (IX).

The reaction temperature of the Heck reaction of Compound (VIII) and Compound (IX) is about 0° C. to about 180° C., preferably about 30° C. to about 110° C.

In addition to the above-described reactions, the transition metal complex of the present invention can be used in asymmetric hydrogenation of α, β-unsaturated ester (e.g., Example 1 described below), asymmetric hydrogenation of olefin or ketone and the like, and thereby an optically active compound which is useful as an intermediate for producing pharmaceuticals can be produced.

The present invention will be explained in more detail below by way of Examples and Reference Examples, but the present invention is not limited to them. Herein, room temperature denotes 10° C. to 35° C. For measuring respective physical properties in Examples, the following instruments were used. $^1$H nuclear magnetic resonance spectrum ($^1$H-NMR): DPX300 (manufactured by Bruker), internal standard substance: tetramethylsilane; $^{13}$C nuclear magnetic resonance spectrum ($^{13}$C-NMR): DPX300 (manufactured by Bruker), internal standard substance: CDCl$_3$; $^{31}$P nuclear magnetic resonance spectrum ($^{31}$P-NMR): DPX300 (manufactured by Bruker), external standard substance: 85% H$_3$PO$_4$ aqueous solution; mass spectroscopy: JMS-700T (manufactured by JEOL. Ltd.); melting point: 530 (manufactured by Buchi).

EXAMPLES

Reference Example 1

(S)-2,2'-bis(trifluoromethanesulfonyloxy)-1,1'-binaphthyl

To a solution of (S)-1,1'-bi-2-naphthol (26.2 g, 91 mmol) in acetonitrile (130 mL) was added pyridine (19.5 g, 2.7 equivalents) at room temperature. Then, trifluoromethanesulfonic anhydride (64.2 g, 2.5 equivalents) was added at 5° C., and the mixture was stirred at 5° C. to 10° C. for 2 hours. After water (100 mL) was added at 3° C. and then ethyl acetate (130 mL) was added, the mixture was stirred at room temperature for 30 minutes. The reaction solution was allowed to separate into layers. An organic layer was washed with water (50 mL) and then concentrated under reduced pressure. To the residue were added diisopropyl ether (150 mL) and active carbon (0.25 g), and the mixture was stirred at 60° C. for 30 minutes. The active carbon was filtered off and the filtrate was concentrated under reduced pressure. The residue was recrystallized from heptane to obtain the title compound (48.9 g, white crystal). Yield 97%.

$^1$H-NMR (300 MHz, CDCl$_3$, TMS) δ: 7.33 (d, 2H, J=8.14 Hz), 7.34–7.46 (m, 2H), 7.57–7.63 (m, 2H), 7.68 (d, 2H, J=9.09 Hz), 8.03 (d, 2H, J=8.23 Hz), 8.16 (d, 2H, J=9.08 Hz).

Reference Example 2

4-Bromo-2,6-di-tert-butylanisole

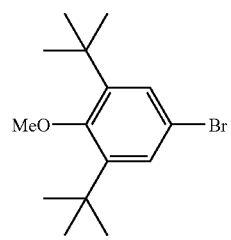

Under argon atmosphere, to a solution of 4-bromo-2,6-di-tert-butylphenol (50 g, 0.175 mol) and potassium carbonate (96.7 g, 4.0 equivalents) in acetone (750 mL) was added dimethyl sulfate (38.6 g, 1.75 equivalents) at 22° C. The mixture was stirred under reflux for 13 hours. Insoluble substances were filtered off and the solvent was distilled off under reduced pressure. By adding ethyl acetate (150 mL) and water (100 mL) to the residue, the reaction mixture was allowed to separate into layers. An organic layer was washed successively with water (100 mL), a 5% NaHCO$_3$ aqueous solution (100 mL) and a 5% NaCl aqueous solution (100 mL), dried over anhydrous magnesium sulfate and then naturally filtered. The filtrate was concentrated under reduced pressure to obtain the title compound (56.1 g, brown oil). Yield 95.2%.

$^1$H-NMR (300 MHz, CDCl$_3$, TMS) δ: 1.41 (s, 18H), 3.68 (s, 3H), 7.33 (s, 2H).

Reference Example 3

Bis(3,5-di-tert-butyl-4-methoxyphenyl)phosphine oxide

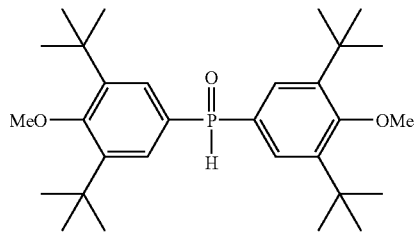

Under argon atmosphere, a solution of magnesium (4.0 g, 0.95 equivalents) and a small amount of iodine in THF (50 mL) was stirred at room temperature for 1 hour. After 4-bromo-2,6-di-tert-butylanisole (52 g, 0.175 mol) synthesized in Reference Example 2 was added at 46° C. to 53° C. thereto, the mixture was stirred at 5° C. for 1 hour. Then, dimethyl phosphite (11.4 g, 0.52 equivalents) was added and the mixture was stirred at 5° C. for 1 hour. After water (50 mL) was added at 3° C. and toluene (50 mL) and 6M-HCl (20 mL) were then added, the mixture was stirred at room temperature for 30 minutes. The reaction solution was allowed to separate into layers. An organic layer was washed successively with water (20 mL), a 5% NaHCO$_3$ aqueous solution (20 mL) and a 5% NaCl aqueous solution (20 mL), dried over anhydrous magnesium sulfate and then naturally filtered. The filtrate was concentrated under reduced pressure. The residue was recrystallized from heptane to obtain the title compound (11.6 g, pale yellowish white crystal). Yield 20.5%, mp. 166.1° C.

$^1$H-NMR (300 MHz, CDCl$_3$, TMS) δ: 1.38 (s, 36H), 3.68 (s, 6H) 7.49 (s, 2H), 7.54 (s, 2H), 8.01 (d, 1H, J=474.4 Hz).
$^{31}$P-NMR (121 MHz, CDCl$_3$, 85% H$_3$PO$_4$) δ: 23.57 (dquint, J=474.1 Hz, 14.0 Hz).

Elementary analysis for C$_{30}$H$_{47}$O$_3$P
Calculated value; C: 74.04; H, 9.73, P: 6.36
Found value; C: 74.13; H, 9.93, P: 6.20.

Reference Example 4

Bis(3,5-di-tert-butyl-4-methoxyphenyl)phosphine-borane complex

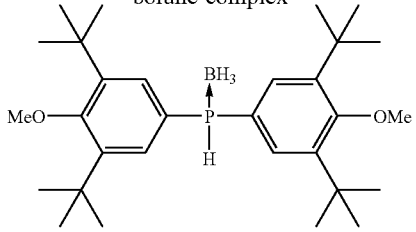

Under argon atmosphere, a solution of cerium chloride (4.55 g, 3.0 equivalents) in THF (25 mL) was stirred at room temperature (25° C.) for 30 minutes. After sodium borohydride (0.72 g, 3.1 equivalents) was added, the mixture was stirred at room temperature for 1 hour. Then, bis(3,5-di-tert-butyl-4-methoxyphenyl)phosphine oxide (3.0 g, 6.16 mmol) synthesized in Reference Example 3 and lithium aluminum hydride (0.28 g, 1.2 equivalents) were successively added at 5° C., and the mixture was stirred at room temperature for 18 hours. After water (10 mL) was added at 3° C. and toluene (30 mL) and 6M-HCl (20 mL) were then added, the mixture was stirred at room temperature for 30 minutes. The reaction solution was allowed to separate into layers. An aqueous layer was extracted with toluene (30 mL). Organic layers were combined, washed with a 5% NaCl aqueous solution (20 mL), dried over anhydrous magnesium sulfate and then naturally filtered. The filtrate was concentrated under reduced pressure. The residue was purified by column chromatography (alumina 25 g, n-hexane). The residue was recrystallized from heptane to obtain the title compound (1.18 g, white crystal). Yield 39.6%, mp. 134.7° C.

$^1$H-NMR (300 MHz, CDCl$_3$, TMS) δ: 0.37–1.08 (m, 3H), 1.39 (s, 36H), 3.69 (s, 6H), 6.23 (dq, 1H, J=376.2 Hz, 6.78 Hz), 7.50 (d, 4H, J=12.18 Hz).

$^{31}$P-NMR (121 MHz, CDCl$_3$, 85% H$_3$PO$_4$) δ: −3.33−−1.46 (m), −0.13−1.80(m).

Reference Example 5
(S)-2,2'-bis[bis(3,5-di-tert-butyl-4-methoxyphenyl)phosphino]-1,1'-binaphthyl

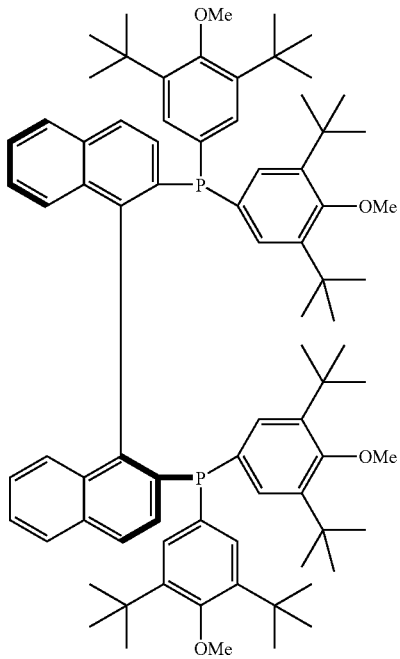

Under argon atmosphere, to a solution (5 mL) of [1,2-bis(diphenylphosphino)-ethane]dichloronickel (48 mg, 0.1 equivalents), (S)-2,2'-bis(trifluoromethanesulfonyloxy)-1,1'-binaphthyl (507 mg, 0.91 mmol) synthesized in Reference Example 1 and 1,4-diazabicyclo[2.2.2]octane (620 mg, 6.0 equivalents) in DMF was added bis(3,5-di-tert-butyl-4-methoxyphenyl)phosphine-borane complex (1.03 g, 2.3 equivalents) synthesized in Reference Example 4 at room temperature. The mixture was stirred at room temperature for 30 minutes and then at 110° C. for 153 hours. DMF was distilled off under reduced pressure. Methanol was added to the residue to obtain the title compound (737 mg, yellowish white crystal). Yield 69%, mp. 129.5° C., Specific Rotation: [α]$_D$=−232° (25° C., c=1.0, CHCl$_3$).

$^1$H-NMR (300 MHz, CDCl$_3$, TMS) δ: 1.21 (s, 36H), 1.24 (s, 36H), 3.58 (s, 6H), 3.64 (s, 6H), 6.64 (d, 2H, J=7.60 Hz), 6.77 (d, 2H, J=7.10 Hz), 6.92–7.00 (m, 4H), 7.13–7.20 (m, 4H), 7.30–7.37 (m, 2H), 7.42–7.51 (m, 2H), 7.77 (d, 2H, J=6.91 Hz), 7.86 (d, 2H, J=8.02 Hz).

$^{13}$C-NMR (75 MHz, CDCl$_3$, CDCl$_3$) δ: 33.34, 33.49, 36.96, 37.19, 65.44, 65.53, 126.64, 127.23, 128.76, 128.80, 128.92, 131.84, 132.95, 134.51, 144.02, 160.37, 161.31.

$^{31}$P-NMR (121 MHz, CDCl$_3$, 85% H$_3$PO$_4$) δ: −15.02 (s).

Mass spectroscopy (ESI-HR); Calculated value; 1189.7332

Found value; 1189.7350 (M-H).

Example 1

Asymmetric Hydrogenation of methyl (Z)-α-acetamidocinnamate

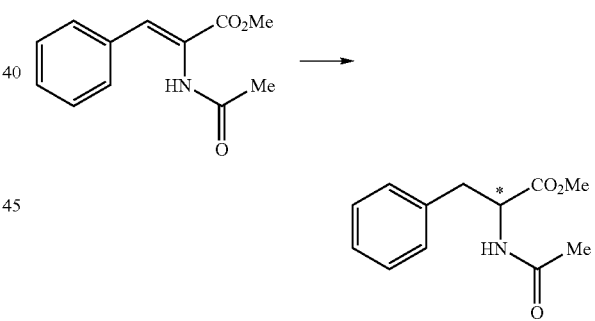

To a solution of Rh(cod)$_2$OTf (4.27 mg, 0.0091 mmol) in methanol (1 mL) was added (S)-2,2'-bis[bis(3,5-di-tert-butyl-4-methoxyphenyl)phosphino]-1,1'-binaphthyl (12.65 mg, 0.011 mmol) synthesized in Reference Example 5, and the mixture was stirred at room temperature (25° C.) for 30 minutes. $^{31}$P-NMR of the reaction mixture was measured ($^{31}$P-NMR (121 MHz, CD$_3$OD, 85% H$_3$PO$_4$) δ: 27.9(s),29.1 (s)). The Rh complex solution thus prepared was added to a solution of methyl (Z)-α-acetamidocinnamate (0.10 g, 0.456 mmol) in methanol (4 mL), and the mixture was subjected to hydrogenation at 25° C. for 24 hours under a hydrogen pressure of 1.0 MPa. The reaction mixture had a conversion rate of >99.9% and an optical purity of 91.43% ee (R), as measured by GC (column: CHIRASIL VAL, 0.25 mm×30 m).

Comparative Example 1

Asymmetric Hydrogenation of methyl (Z)-α-acetamidocinnamate

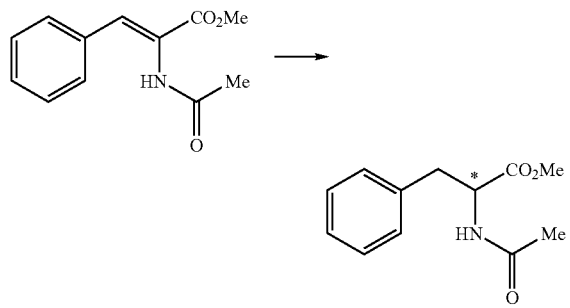

To a solution of Rh(cod)$_2$OTf (4.27 mg, 0.0091 mmol) in methanol (1 mL) was added (S)-2,2'-bis(diphenylphosphino)-1,1'-binaphthyl (6.79 mg, 0.011 mmol), and the mixture was stirred at room temperature (25° C.) for 30 minutes. The Rh complex solution thus prepared was added to a solution of methyl (Z)-α-acetamidocinnamate (0.10 g, 0.456 mmol) in methanol (4 mL), and the mixture was subjected to hydrogenation at 25° C. for 24 hours under a hydrogen pressure of 1.0 MPa. The reaction mixture had a conversion rate of >99.9% and an optical purity of 15.33% ee (R), as measured by GC (column: CHIRASIL VAL, 0.25 mm×30 m).

Example 2

Synthesis of diacetato{(S)-2,2'-bis[bis(3,5-di-tert-butyl-4-methoxyphenyl)phosphino]-1,1'-binaphthyl}ruthenium(II)

Under argon atmosphere, N,N-dimethylformamide (4 mL) was added to bis (η$^6$-benzene)-tetra-μ-chloro diruthenium(II) (100.0 mg, 0.200 mmol) and (S)-2,2'-bis[bis(3,5-di-tert-butyl-4-methoxyphenyl)phosphino]-1,1'-binaphthyl (453.1 mg, 0.380 mmol) synthesized in Reference Example 5, and the mixture was stirred at 100° C. for 10 minutes. The solvent of the reaction solution was distilled off. A solution of sodium acetate (640.4 mg, 7.80 mmoL) in methanol (6 mL) was added to the residue, and the mixture was reacted under ultrasonic irradiation for 20 minutes. By adding toluene (3 mL) and water (6 mL), the reaction solution was allowed to separate into layers. Toluene (3 mL) was added to an aqueous layer and it was allowed to separate into layers. Water (6 mL) was added to combined organic layers and the resulting mixture was allowed to separate into layers. The solvent of an organic layer was distilled off. Toluene (1 mL) and methanol (6 mL) were added to the residue. After the mixture was allowed to stand at room temperature for 15 hours and then at 4° C. for 5 days, insoluble substances were filtered. From the filtrate, the title compound (450 mg, brown powder) was obtained. Yield 80%.

$^1$H-NMR (300 MHz, CD$_2$Cl$_2$, TMS) δ: 1.0 (s, 36H), 1.3 (s, 36H), 1.5 (s, 6H), 3.2 (s, 6H), 3.7 (s, 6H), 6.0 (d, 2H, J=8.4 Hz), 6.6–6.7 (m, 2H), 6.9 (t, 4H, J=5.6 Hz), 7.0–7.1 (m, 2H), 7.3–7.4 (m, 4H), 7.5 (d, 2H, J=8.1 Hz), 7.6 (d, 2H, J=8.5 Hz), 7.8–7.9 (m, 2H).

$^{31}$P-NMR (121 MHz, CD$_2$Cl$_2$, 85% H$_3$PO$_4$) δ: 67.5 (s).

Example 3

Synthesis of {[(S)-2,2'-bis[bis(3,5-di-tert-butyl-4-methoxyphenyl)phosphino]-1,1'-binaphthyl]dichloro ruthenium(II)}(N,N-dimethylformamide)$_n$ Under argon atmosphere, N,N-dimethylformamide (4 mL) was added to bis (η$^6$-benzene)-tetra-μ-chlorodiruthenium(II) (101.7 mg, 0.203 mmol) and (S)-2,2'-bis[bis(3,5-di-tert-butyl-4-methoxyphenyl)phosphino]-1,1'-binaphthyl (454.8 mg, 0.382 mmol) synthesized in Reference Example 5, and the mixture was stirred at 100° C. for 60 minutes. The solvent of the reaction solution was distilled off to obtain the title compound (469 mg, reddish brown powder). Yield 80%. $^{31}$P-NMR (121 MHz, CD$_2$Cl$_2$, 85% H$_3$PO$_4$) δ: 56.8 (s), 70.1 (s).

Example 4

Synthesis of {(S)-2,2'-bis[bis(3,5-di-tert-butyl-4-methoxyphenyl)phosphino]-1,1'-binaphthyl}dichloro ruthenium(II)

Under argon atmosphere, 5% hydrochloric acid-methanol (0.3 mL) was added to a solution of diacetato{(S)-2,2'-bis[bis(3,5-di-tert-butyl-4-methoxyphenyl)phosphino]-1,1'-binaphthyl}ruthenium(II) (237 mg, 0.168 mmol) synthesized in Example 2 in methylene chloride (4 mL), and the mixture was stirred at room temperature for 93 hours. The solvent of the reaction solution was distilled off to obtain the title compound (22 mg, brown powder). Yield 96%.

$^{31}$P-NMR (121 MHz, CD$_2$Cl$_2$, 85% H$_3$PO$_4$) δ: 62.2 (s).

Example 5

Asymmetric Hydrogenation of 2-chloro-3-oxo-3-phenyl-propionic acid ethyl ester

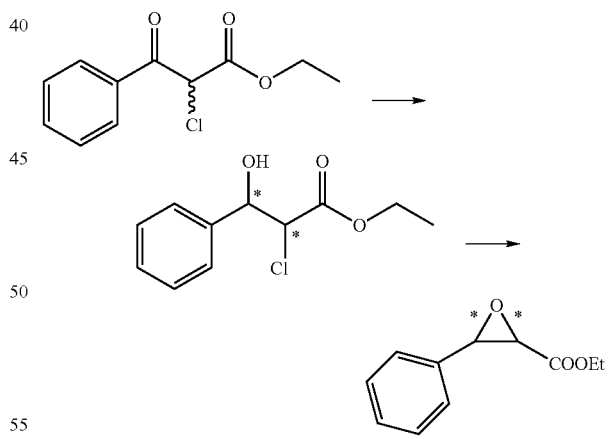

A solution of diacetato{(S)-2,2'-bis[bis(3,5-di-tert-butyl-4-methoxyphenyl)phosphino]-1,1'-binaphthyl}ruthenium (II) (30.1 mg, 0.021 mmol) synthesized in Example 2 and 2-chloro-3-oxo-3-phenyl-propionic acid ethyl ester (0.966 g, 4.261 mmol) in ethanol (9 mL) was hydrogenated at 80° C. under a hydrogen pressure of 1 MPa for 17.5 hours. The reaction mixture had a conversion rate of >99.9% as measured by GC (column: α-DEX 120, 0.25 mm×30 m). Further, the solvent of the reaction mixture was distilled off. To the residue were added N,N-dimethylformamide (water content: 1.8%, 18 mL) and potassium carbonate (1.79 g, 13.0 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 77.5% ee (2R,3R) and 82.7% de (cis) as measured by GC (column: α-DEX 120, 0.25 mm×30 m).

Comparative Example 2

Asymmetric Hydrogenation of 2-chloro-3-oxo-3-phenyl-propionic acid ethyl ester

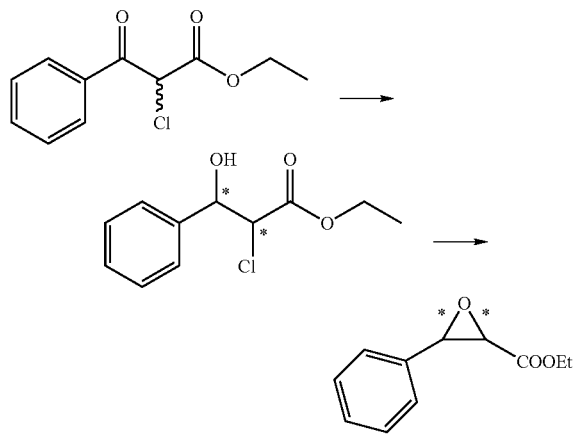

A solution of diacetato{(R)-2,2'-bis(diphenylphosphino)-1,1'-binaphthyl}ruthenium(II) (30.6 mg, 0.036 mmol) and 2-chloro-3-oxo-3-phenyl-propionic acid ethyl ester (1.62 g, 7.17 mmol) in ethanol (15 mL) was hydrogenated at 80° C. under a hydrogen pressure of 1 MPa for 17.5 hours. The reaction mixture had a conversion rate of >99.9% as measured by GC (column: α-DEX 120, 0.25 mm×30 m). Further, the solvent of the reaction mixture was distilled off. To the residue were added N,N-dimethylformamide (water content: 1.8%, 30 mL) and potassium carbonate (2.98 g, 21.56 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 3.9% ee (2R, 3R) and 85.7% de (cis) as measured by GC (column: α-DEX 120, 0.25 mm×30 m).

Example 6

Asymmetric Hydrogenation of 2-chloro-3-oxo-3-phenyl-propionic acid ethyl ester

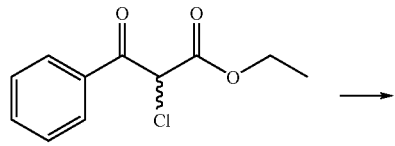

-continued

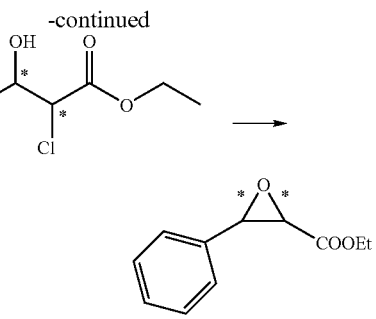

A solution (10 mL) of 2-chloro-3-oxo-3-phenyl-propionic acid ethyl ester (1.57 g, 6.928 mmol) in ethanol was added to a solution (5 mL) of {[(S)-2,2'-bis[bis(3,5-di-tert-butyl-4-methoxyphenyl)phosphino]-1,1'-binaphthyl]dichlororuthenium(II)}(N,N-dimethylformamide)$_n$ (50.5 mg, 0.036 mmol) synthesized in Example 3 in ethanol. The mixture was hydrogenated at 80° C. under a hydrogen pressure of 1 MPa for 16.5 hours. The reaction mixture had a conversion rate of >99.9% as measured by GC (column: α-DEX 120, 0.25 mm×30 m). Further, the solvent of the reaction mixture was distilled off. To the residue were added N,N-dimethylformamide (water content: 1.8%, 30 mL) and potassium carbonate (2.90 g, 20.9 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 79.4% ee (2R, 3R) and 82.4% de (cis) as measured by GC (column: α-DEX 120, 0.25 mm×30 m).

Comparative Example 3

Asymmetric Hydrogenation of 2-chloro-3-oxo-3-phenyl-propionic acid ethyl ester

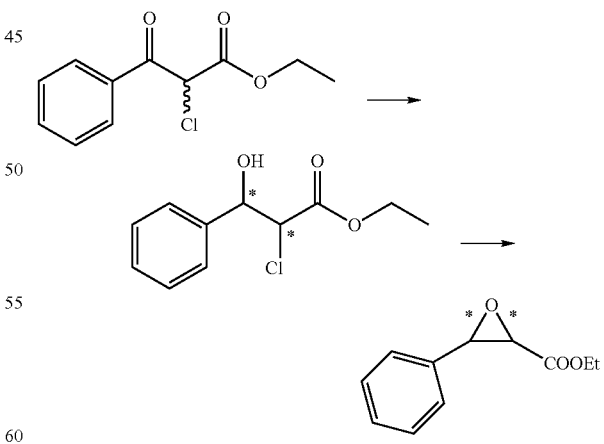

A solution of {[(R)-2,2'-bis(diphenylphosphino)-1,1'-binaphthyl]-dichlororuthenium(II)}(N,N-dimethylformamide)$_n$ (27.8 mg, 0.033 mmol) and 2-chloro-3-oxo-3-phenyl-propionic acid ethyl ester (1.586 g, 6.998 mmol) in ethanol (15 mL) was hydrogenated at 80° C. under a hydrogen pressure of 1 MPa for 16.5 hours. The reaction mixture had a conversion rate of >99.9% as measured by GC (column: α-DEX 120, 0.25 mm×30 m). Further, the solvent of the reaction mixture was distilled off. To the residue were added N,N-dimethylformamide (water content: 1.8%, 30 mL) and potassium carbonate (2.95 g, 21.3 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 4.5% ee (2R, 3R) and 87.7% de (cis) as measured by GC (column: α-DEX 120, 0.25 mm×30 m).

Example 7

Asymmetric Hydrogenation of 2-chloro-3-oxo-3-phenyl-propionic acid ethyl ester

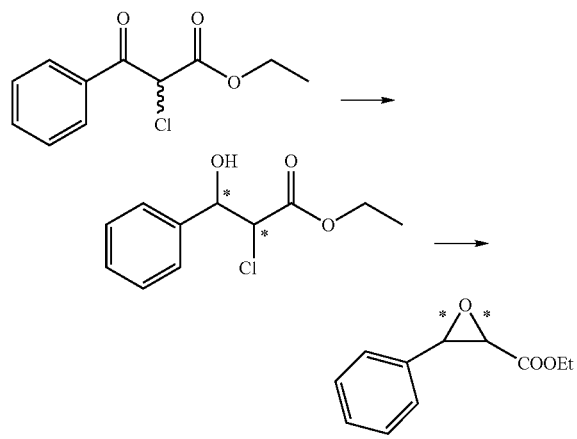

Under argon atmosphere, triethylamine (0.3 mL) was added to a solution of dichloro($\eta^2,\eta^2$-1,5-cyclooctadiene)ruthenium(II) (100.9 mg, 0.396 mmol) and (S)-2,2'-bis[bis(3,5-di-tert-butyl-4-methoxyphenyl)phosphino]-1,1'-binaphthyl (467.0 mg, 0.392 mmol) synthesized in Reference Example 5 in toluene (6 mL). The mixture was refluxed under stirring at 135° C. for 3 hours. The solvent of the reaction solution was distilled off to obtain a brown powder (440 mg). A solution of the brown powder thus obtained (50.0 mg, 0.035 mmol) and 2-chloro-3-oxo-3-phenyl-propionic acid ethyl ester (1.61 g, 7.12 mmol) in ethanol (15 mL) was hydrogenated at 80° C. under a hydrogen pressure of 1 MPa for 15 hours. The reaction mixture had a conversion rate of 86.5% as measured by GC (column: α-DEX 120, 0.25 mm×30 m). Further, the solvent of the reaction mixture was distilled off. To the residue were added N,N-dimethylformamide (water content: 1.8%, 30 mL) and potassium carbonate (2.93 g, 21.2 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 85.1% ee (2R, 3R) and 87.8% de (cis) as measured by GC (column: α-DEX 120, 0.25 mm×30 m).

Comparative Example 4

Asymmetric Hydrogenation of 2-chloro-3-oxo-3-phenyl-propionic acid ethyl ester

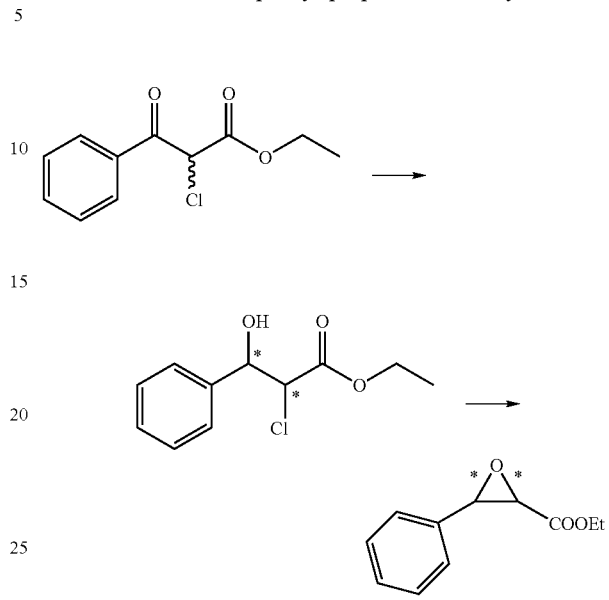

A solution of a ruthenium-[(R)-2,2'-bis(diphenylphosphino)-1,1'-binaphthyl] complex (33.6 mg, 0.040 mmol) synthesized in a similar manner to Example 7 and 2-chloro-3-oxo-3-phenyl-propionic acid ethyl ester (1.64 g, 7.24 mmol) in ethanol (15 mL) was hydrogenated at 80° C. under a hydrogen pressure of 1 MPa for 15 hours. The reaction mixture had a conversion rate of >99.9% as measured by GC (column: α-DEX 120, 0.25 mm×30 m). Further, the solvent of the reaction mixture was distilled off. To the residue were added N,N-dimethylformamide (water content: 1.8%, 30 mL) and potassium carbonate (3.02 g, 21.9 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 3.1% ee (2R, 3R) and 86.6% de (cis) as measured by GC (column: α-DEX 120, 0.25 mm×30 m).

Example 8

Asymmetric Hydrogenation of 2-chloro-3-oxo-3-phenyl-propionic acid ethyl ester

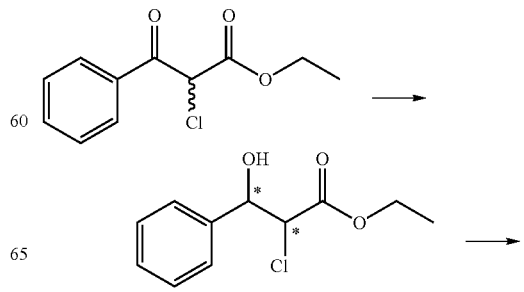

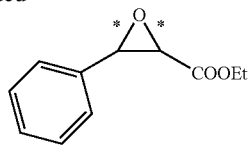

A solution of (S)-2,2'-bis[bis(3,5-di-tert-butyl-4-methoxyphenyl)phosphino]-1,1'-binaphthyl (54.7 mg, 0.046 mmol) synthesized in Reference Example 5, ($\eta^2,\eta^2$-1,5-cyclooctadiene)bis-(2-methylallyl)ruthenium(II) (12.8 mg, 0.040 mmol) and 2-chloro-3-oxo-3-phenyl-propionic acid ethyl ester (1.71 g, 7.53 mmol) in ethanol (15 mL) was hydrogenated at 80° C. under a hydrogen pressure of 1 MPa for 14 hours. The reaction mixture had a conversion rate of 4.6% as measured by GC (column: α-DEX 120, 0.25 mm×30 m). Further, the solvent of the reaction mixture was distilled off. To the residue were added N,N-dimethylformamide (water content: 1.8%, 18 mL) and potassium carbonate (3.15 g, 22.8 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 67.6% ee (2R, 3R) and 69.1% de (cis) as measured by GC (column: α-DEX 120, 0.25 mm×30 m).

Comparative Example 5

Asymmetric Hydrogenation of 2-chloro-3-oxo-3-phenyl-propionic acid ethyl ester

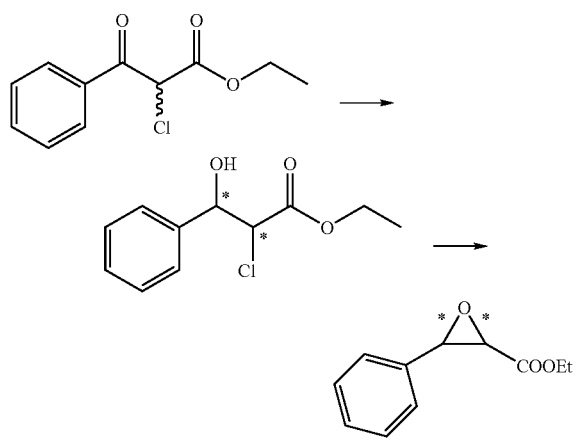

A solution of (R)-2,2'-bis(diphenylphosphino)-1,1'-binaphthyl (30.3 mg, 0.049 mmol), ($\eta^2,\eta^2$-1,5-cyclooctadiene)bis-(2-methylallyl)ruthenium(II) (13.6 mg, 0.042 mmol) and 2-chloro-3-oxo-3-phenyl-propionic acid ethyl ester (1.71 g, 7.543 mmol) in ethanol (15 mL) was hydrogenated at 80° C. under a hydrogen pressure of 1 MPa for 14 hours. The reaction mixture had a conversion rate of >99.9% as measured by GC (column: α-DEX 120, 0.25 mm×30 m). Further, the solvent of the reaction mixture was distilled off. To the residue were added N,N-dimethylformamide (water content: 1.8%, 18 mL) and potassium carbonate (3.18 g, 23.0 mmol) and the mixture was stirred for 6 hours. By addition of isopropyl ether (30 mL) and water (30 mL), the mixture was extracted and allowed to separate into layers. Isopropyl ether (30 mL) was added to an aqueous layer and it was extracted again. Combined organic layers were washed successively with 1N hydrochloric acid (30 mL), water (30 mL) and water (30 mL). The resulting organic layer had an optical purity of 1.1% ee (2S, 3S) and 84.9% de (cis) as measured by GC (column: α-DEX 120, 0.25 mm×30 m).

Example 9

Asymmetric Heck Reaction

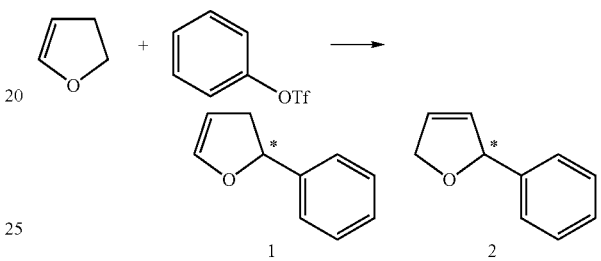

To a solution of palladium(II) acetate (2.2 mg, 0.0099 mmol) in 1,4-dioxane (2.5 mL) were added diisopropylethylamine (0.25 mL, 11.46 mmol) and (S)-2,2'-bis[bis(3,5-di-tert-butyl-4-methoxyphenyl)phosphino]-1,1'-binaphthyl (35.6 mg, 0.030 mmol) synthesized in Reference Example 5, and the mixture was stirred at 60° C. for 1 hour. $^{31}$P-NMR of the reaction mixture was measured ($^{31}$P-NMR (121 MHz, CDCl$_3$, 85% H$_3$PO$_4$) δ: 29.24–29.54 (m)). To the reaction mixture were successively added 2,3-dihydrofuran (0.19 mL, 2.50 mmol) and phenyl trifluoromethanesulfonate (0.079 mL, 0.488 mmol) and the mixture was reacted at 105° C. for 24 hours. The reaction mixture had a conversion rate of >99.9%, an optical purity of 64.9% ee(S) and a production ratio (1/2) of 33:1, as measured by GC (column: CP-Chirasil-DEX CB, 0.32 mm×25 m).

Comparative Example 6

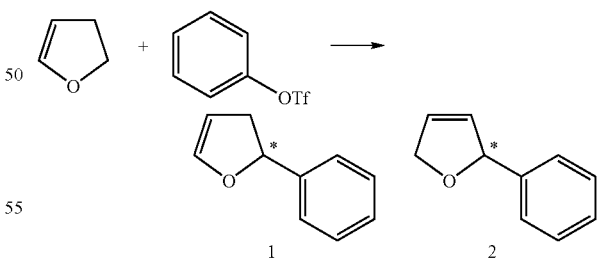

To a solution of palladium(II) acetate (2.2 mg, 0.0099 mmol) in 1,4-dioxane (2.5 mL) were added diisopropylethylamine (0.25 mL, 11.46 mmol) and (S)-2,2'-bis(diphenylphosphino)-1,1'-binaphthyl (18.6 mg, 0.030 mmol), and the mixture was stirred at 60° C. for 1 hour. To the mixture were successively added 2,3-dihydrofuran (0.19 mL, 2.50 mmol) and phenyl trifluoromethanesulfonate (0.079 mL, 0.488 mmol) and the mixture was reacted at 105° C. for 24 hours. The reaction mixture had a conversion rate of >99.9%, an optical purity of 48.8% ee (S) and a production ratio (1/2) of 6:1, as measured by GC (column: CP-Chirasil-DEX CB, 0.32 mm×25 m)

INDUSTRIAL APPLICABILITY

By using the transition metal complex with 2,2'-bis[bis(3,5-di-tert-butyl-4-methoxyphenyl)phosphino]-1,1'-binaphthyl as a ligand of the present invention in asymmetric reaction (particularly, asymmetric reduction), a compound having an objective absolute configuration can be efficiently obtained.

The invention claimed is:

1. A transition metal complex with 2,2'-bis[bis(3,5-di-tert-butyl-4-methoxyphenyl)phosphino]-1,1'-binaphthyl as a ligand.

2. The transition metal complex according to claim 1, wherein the transition metal is rhodium, ruthenium, iridium, palladium, nickel or copper.

3. The transition metal complex according to claim 1, wherein the transition metal is rhodium, ruthenium, iridium, palladium or nickel.

4. The transition metal complex according to claim 1, wherein the transition metal is rhodium.

5. The transition metal complex according to claim 1, wherein the transition metal is ruthenium.

6. The transition metal complex according to claim 1, which is represented by $Ru(L)(AcO)_2$ wherein L denotes 2,2'-bis[bis(3,5-di-tert-butyl-4-methoxyphenyl)phosphino]-1,1'-binaphthyl and Ac denotes acetyl.

7. The transition metal complex according to claim 1, which is represented by $Ru(L)Cl_2$ wherein L denotes 2,2'-bis[bis(3,5-di-tert-butyl-4-methoxyphenyl)phosphino]-1,1'-binaphthyl.

8. The transition metal complex according to claim 1, which is represented by $Ru(L)Cl_2(dmf)_n$ wherein L denotes 2,2'-bis[bis(3,5-di-tert-butyl-4-methoxyphenyl)phosphino]-1,1'-binaphthyl and dmf denotes N,N-dimethylformamide.

9. The transition metal complex according to claim 1, which is represented by $[Rh(L)(cod)]OTf$ wherein L denotes 2,2'-bis[bis(3,5-di-tert-butyl-4-methoxyphenyl)phosphino]-1,1'-binaphthyl, cod denotes 1,5-cyclooctadiene, and Tf denotes trifluoromethylsulfonyl.

10. A process for preparing a compound represented by the formula:

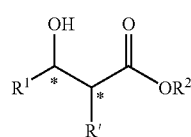

wherein * denotes the position of asymmetric carbon and the other symbols are as defined below, or a salt thereof, which comprises reducing a compound represented by the formula:

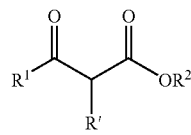

wherein $R^1$ denotes an optionally substituted hydrocarbon group or an optionally substituted heterocyclic group, R' denotes a halogen atom, optionally substituted alkylsulfonyloxy or optionally substituted arylsulfonyloxy, and $R^2$ denotes an optionally substituted hydrocarbon group, or a salt thereof in the presence of a transition metal complex with 2,2'-bis[bis(3,5-di-tert-butyl-4-methoxyphenyl)phosphino]-1,1'-binaphthyl as a ligand.

11. A process for preparing a compound represented by the formula:

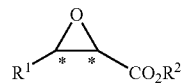

wherein respective symbols are as defined below, or a salt thereof, which comprises reducing a compound represented by the formula:

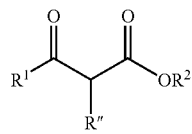

wherein $R^1$ denotes an optionally substituted hydrocarbon group or an optionally substituted heterocyclic group, R" denotes a chlorine atom, a bromine atom, an iodine atom, optionally substituted alkylsulfonyloxy or optionally substituted arylsulfonyloxy, and $R^2$ denotes an optionally substituted hydrocarbon group, or a salt thereof in the presence of a transition metal complex in a solvent selected from an alcohol solvent, a hydrocarbon solvent, an ether solvent, an ester solvent, a ketone solvent, a nitrile solvent, a sulfoxide solvent and an amide solvent, or a mixed solvent of two or more kinds of them, to obtain a compound represented by the formula:

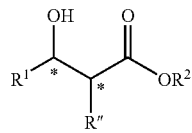

wherein * denotes the position of asymmetric carbon and the other symbols are as defined above, or a salt thereof, and then cyclizing the resulting compound in the presence of an inorganic base.

12. The process according to claim 11, wherein the compound represented by the formula:

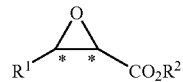

wherein $R^1$ denotes an optionally substituted hydrocarbon group or an optionally substituted heterocyclic group, $R^2$ denotes an optionally substituted hydrocarbon group, and * denotes the position of asymmetric carbon, is an optically active compound represented by the formula:

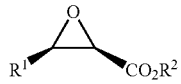

wherein respective symbols are as defined above, or the formula:

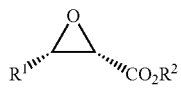

wherein respective symbols are as defined above.

13. The process according to claim 11, wherein the compound represented by the formula:

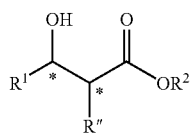

wherein $R^1$ denotes an optionally substituted hydrocarbon group or an optionally substituted heterocyclic group, R" denotes a chlorine atom, a bromine atom, an iodine atom, optionally substituted alkylsulfonyloxy or optionally substituted arylsulfonyloxy, $R^2$ denotes an optionally substituted hydrocarbon group, and * denotes the position of asymmetric carbon, is an optically active compound represented by the formula:

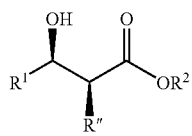

wherein respective symbols are as defined above, or the formula:

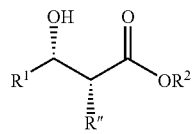

wherein respective symbols are as defined above.

14. The process according to claim 11, wherein R" is a chlorine atom, a bromine atom or an iodine atom.

15. The process according to claim 11, wherein the inorganic base is alkali metal carbonate.

16. The process according to claim 11, wherein the solvent for reduction is an alcohol solvent.

17. The process according to claim 11, wherein the transition metal complex is a transition metal complex with 2,2'-bis[bis(3,5-di-tert-butyl-4-methoxyphenyl)phosphino]-1,1'-binaphthyl as a ligand.

18. A process for preparing a compound represented by the formula:

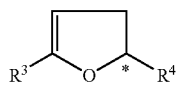

wherein * denotes the position of asymmetric carbon and the other symbols are as defined below, or a salt thereof, which comprises reacting a compound represented by the formula:

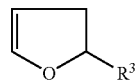

wherein $R^3$ denotes a hydrogen atom or optionally substituted alkyl, or a salt thereof with a compound represented by the formula: $R^4$—R''' wherein $R^4$ denotes optionally substituted phenyl and R''' denotes a leaving group, or a salt thereof in the presence of a transition metal complex with 2,2'-bis[bis(3,5-di-tert-butyl-4-methoxyphenyl)phosphino]-1,1'-binaphthyl as a ligand.

* * * * *